United States Patent
Lee et al.

(10) Patent No.: US 10,756,389 B2
(45) Date of Patent: Aug. 25, 2020

(54) METHOD FOR THE MANUFACTURE OF FLUORINATED CYCLIC CARBONATES AND THEIR USE FOR LITHIUM ION BATTERIES

(71) Applicant: SOLVAY SA, Brussels (BE)

(72) Inventors: Ji-hun Lee, Seoul (KR); Ji-Ae Choi, Seoul (KR); Hyung Kwon Hwang, Gyeonggi-do (KR); Martin Bomkamp, Hannover (DE); Sergey N. Tverdomed, Bremen (DE); Mykhailo Shevchuk, Bremen (DE); Nataliya Kalinovich, Bremen (DE); Gerd-Volker Röschenthaler, Bremen (DE)

(73) Assignee: SOLVAY SA, Brussels (BE)

( * ) Notice: Subject to any disclaimer, the term of this patent is extended or adjusted under 35 U.S.C. 154(b) by 163 days.

(21) Appl. No.: 15/747,496

(22) PCT Filed: Jul. 28, 2016

(86) PCT No.: PCT/EP2016/068056
§ 371 (c)(1),
(2) Date: Jan. 25, 2018

(87) PCT Pub. No.: WO2017/017210
PCT Pub. Date: Feb. 2, 2017

(65) Prior Publication Data
US 2018/0219256 A1    Aug. 2, 2018

(30) Foreign Application Priority Data
Jul. 29, 2015 (EP) .................................... 15178921

(51) Int. Cl.
*H01M 12/08* (2006.01)
*H01M 10/0567* (2010.01)
(Continued)

(52) U.S. Cl.
CPC ...... H01M 10/0567 (2013.01); C07D 317/22 (2013.01); C07D 317/34 (2013.01);
(Continued)

(58) Field of Classification Search
CPC ............ H01M 10/0567; H01M 12/08; H01M 10/0525; H01M 10/052; H01M 2300/025; C07D 317/22; C07D 317/34; H01G 11/64; H01G 11/62; H01G 11/60; H01G 11/54; Y02E 60/13
See application file for complete search history.

(56) References Cited

U.S. PATENT DOCUMENTS

2006/0134528 A1 * 6/2006 Ihara ................. H01M 10/0525
429/329
2010/0062344 A1   3/2010 Koh et al.
2013/0089779 A1   4/2013 Ihara et al.

OTHER PUBLICATIONS

Katzhandler et al. J. Chem. Soc. Perkin Trans. II 1989 pp. 1729-1739 (Year: 1989).*

(Continued)

*Primary Examiner* — Lisa S Park

(57) ABSTRACT

The present invention concerns methods for the manufacture of ethylene carbonate substituted with a fluorinated alkoxy group, certain ethylene carbonates substituted with a fluorinated alkoxy group as well as their use as solvent or solvent additive for lithium ion batteries and supercapacitors.

20 Claims, 2 Drawing Sheets

(51) Int. Cl.
*H01M 10/0525* (2010.01)
*H01M 10/052* (2010.01)
*H01G 11/64* (2013.01)
*H01G 11/62* (2013.01)
*H01G 11/60* (2013.01)
*C07D 317/22* (2006.01)
*C07D 317/34* (2006.01)

(52) U.S. Cl.
CPC .............. *H01G 11/60* (2013.01); *H01G 11/62* (2013.01); *H01G 11/64* (2013.01); *H01M 10/052* (2013.01); *H01M 10/0525* (2013.01); *H01M 12/08* (2013.01); *H01M 2300/0025* (2013.01); *Y02E 60/13* (2013.01)

(56) References Cited

OTHER PUBLICATIONS

Araki, Y. et al., "Synthetic Studies of Carbohydrate Derivatives by Photochemical Reactions, Part 16. Synthesis of DL-Apiose Derivatives by Photochemical Cycloaddition of 1, 3-Dihydroxypropan-2-one Derivatives with Ethenediol or Ethanol Derivatives", Journal of the Chemical Society Perkin Transactions 1 Organic and Bio-Organic Chemistry, 1981, pp. 12-23.

Katzhendler, J. et al, "Conformational Studies of Substituted Five-membered Cyclic Carbonates and Related compounds by MNDO, and the X-Ray Crystal Structure of 4-Chloro-phenyloxymethyl-1, 3-dioxolan-2-one", J. Chem. Soc. Perkin Trans II, 1989, pp. 1729-1739.

Kolomeitsev, A. A. et al, "Versatile application of trifluoromethyl triflate", Tetrahedron Letters 49, 2008, pp. 449-454.

\* cited by examiner

METHOD FOR THE MANUFACTURE OF FLUORINATED CYCLIC CARBONATES AND THEIR USE FOR LITHIUM ION BATTERIES

This application is a U.S. national phase entry under 35 U.S.C. § 371 of International Application No. PCT/EP2016/068056, filed on Jul. 28, 2016, which claims priority to European Application No. 15178921.1, filed on Jul. 29, 2015. The entire contents of these applications are explicitly incorporated herein by this reference.

FIELD OF THE INVENTION

The present invention concerns methods for the manufacture of ethylene carbonate substituted with a fluorinated alkoxy group, certain ethylene carbonates substituted with a fluorinated alkoxy group as well as their use as solvent or solvent additive for lithium ion batteries and supercapacitors.

BACKGROUND OF THE INVENTION

Lithium ion batteries, lithium air batteries and lithium sulfur batteries are well-known rechargeable devices for storing electric energy. Lithium ion batteries comprise an electrolyte composition containing a solvent, a conductive salt and, often, additives. The solvent is an aprotic organic solvent which serves to dissolve the conductive salt. See, for example, WO 2007/042471 which provides information concerning suitable solvents. Suitable conductive salts are known in the art. $LiPF_6$ is a preferred conductive salt.

Capacitors are widely used devices for storing electrical energy. Among the various types of capacitors are electrochemical capacitors and electrolytic capacitors.

A hybrid supercapacitor is an electrochemical energy storage device that employs two different electrode types, the difference between the electrodes generally being in capacity or composition, and an electrolyte composition.

The optimization of the electrolyte compositions in hybrid supercapacitors still offers a significant potential to improve the performance properties of such systems.

Additives improve the properties of lithium ion batteries, e.g. by extending the cycle life. Fluoroalkyl alkyl carbonates, e.g. fluoromethyl methyl carbonate, and fluorinated alkyl carbamates are known solvent additives for lithium ion batteries. WO 2011/006822 discloses the manufacture of 1-fluoroalkyl (fluoro) alkyl carbonates and carbamates. However, there is still a demand in the art for improved additives for lithium ion batteries as well as for improved methods for the manufacture of additives.

Accordingly, the objective of the present invention is to provide methods for the manufacture of fluorinated cyclic carbonates that are advantageous in terms of overall yield and/or purity of the desired product, the energy consumption of the manufacturing process, the safety requirements of the process, the ease of work-up, and/or the side-product profile.

Furthermore, it is an objective of the present invention to provide improved additives for lithium ion batteries, lithium air batteries, lithium sulphur batteries or supercapacitors. The compounds of the present invention provide advantages like modifying the viscosity or reducing the flammability. Another advantage is the modification of the electrodes under formation of beneficial films or a solid electrolyte interphase (SEI). Furthermore, the compounds of the invention advantageously lead to a better wettability of materials used in lithium ion batteries such as in particular a separator. The compounds of the invention can suitably assist in the protection against over-charging, for example, by serving as a redox shuttle. Yet another advantage is an increase in stability of the electrolyte composition, e.g. in presence of copper substrate, which can be formed by possible degradation of certain current collector materials.

Furthermore, the compounds of the present invention advantageously show a higher stability towards reduction and/or oxidation. Alternatively, the compounds of the present invention advantageously show a high stability towards oxidation while having a relatively low stability towards reduction. This property can lead to an increased performance of the battery, e.g. by modifying the electrodes of the battery, specifically by the formation on a protective layer on the electrode. The inventive products can also advantageously lead to an improved performance when used together with a silicon anode in a lithium ion battery. Additionally, the inventive products advantageously allow the voltage of the batteries comprising electrolytes comprising products to be higher, preferably equal or higher than 4.4 V.

Additionally, the compounds of the present invention may increase energy density of a supercapacitor, their power density or their cycle life.

SUMMARY OF THE INVENTION

Accordingly, the present invention concerns in a first aspect a method for the manufacture of a compound of general formula (I),

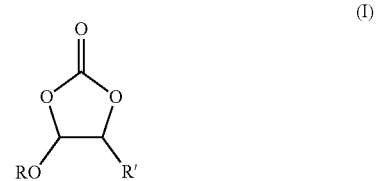

(I)

wherein R is fluorosubstituted alkyl or fluorosubstituted alkyloxyalkylene and R' is hydrogen, fluorine, alkyl, fluorosubstituted alkyl or fluorosubstituted alkyloxyalkylene; comprising a step of reacting a compound of general formula (II),

(II)

wherein R' has the meaning as given above; with a compound of general formula R—OH or a compound of general formula R—O⁻M⁺, wherein R has the meaning as given above and M⁺ is an alkaline metal cation, an alkaline earth metal cation equivalent with one positive charge, an ammonium ion or a guanidinium ion.

In a second aspect, the present invention relates to a method for the manufacture of a compound of general formula (I),

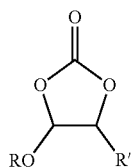

(I)

wherein R is fluorosubstituted alkyl or fluorosubstituted alkyloxyalkylene and R' is hydrogen, fluorine, alkyl, fluorosubstituted alkyl or fluorosubstituted alkyloxyalkylene; comprising a step of reacting a compound of general formula (III),

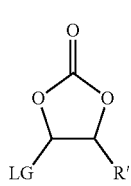

(III)

wherein R' has the meaning as given above and LG is a leaving group; with a compound of general formula R—OH or a compound of general formula R—O⁻M⁺, wherein R has the meaning as given above and M⁺ is an alkaline metal cation, an alkaline earth metal cation equivalent with one positive charge, an ammonium ion or a guanidinium ion.

In a third aspect, the present invention relates to compounds of general formula (IV),

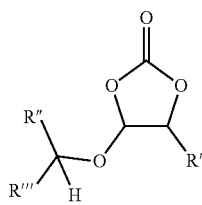

(IV)

wherein R' is hydrogen, fluorine, alkyl, fluorosubstituted alkyl or fluorosubstituted alkyloxyalkylene; R" is fluorosubstituted alkyl or fluorosubstituted alkyloxyalkylene and R'" is hydrogen, fluorine, alkyl, fluorosubstituted alkyl or fluorosubstituted alkyloxyalkylene.

DETAILED DESCRIPTION OF THE INVENTION

Figure 1:
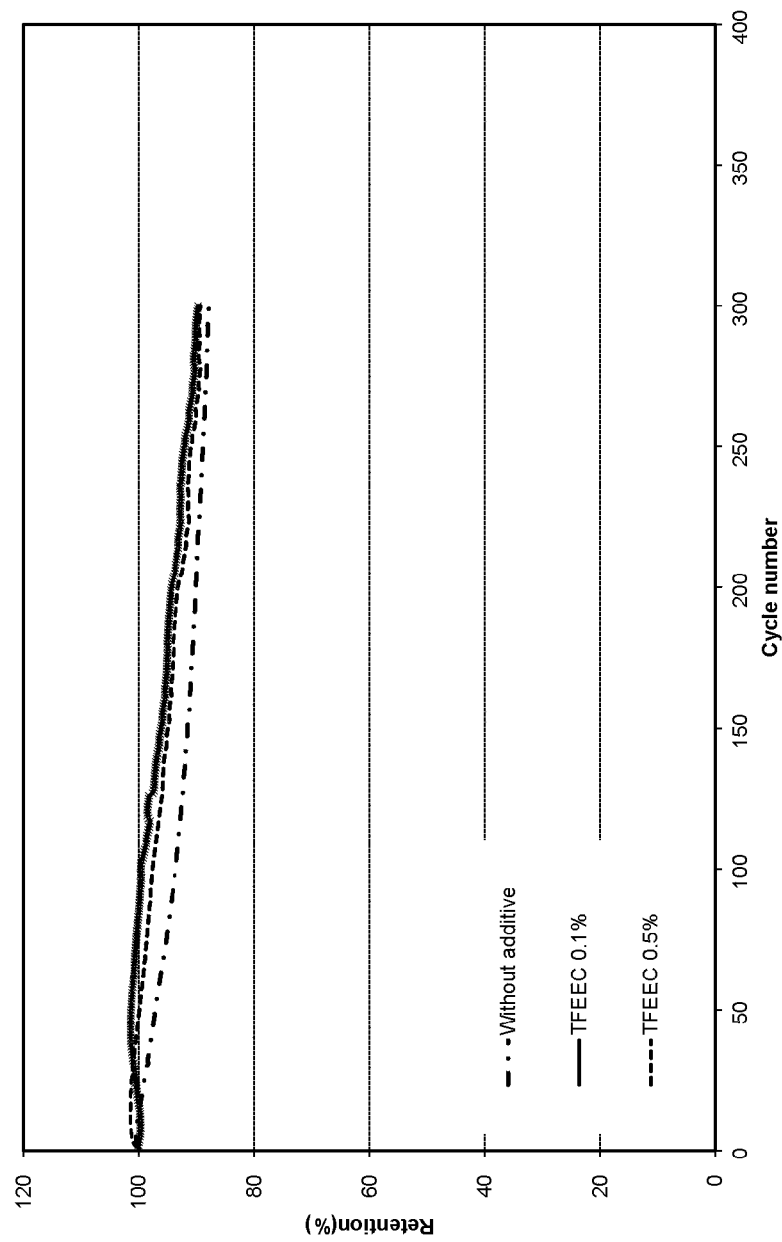
FIG. 1 shows the results of the cycle performance test based on mono full cells system described in Example 5 of lithium-ion cells comprising a compound according to the invention.

The present invention concerns in a first aspect a method for the manufacture of a compound of general formula (I),

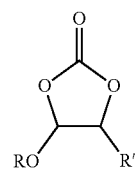

(I)

wherein R is fluorosubstituted alkyl or fluorosubstituted alkyloxyalkylene and R' is hydrogen, fluorine, alkyl, fluorosubstituted alkyl or fluorosubstituted alkyloxyalkylene; comprising a step of reacting a compound of general formula (II),

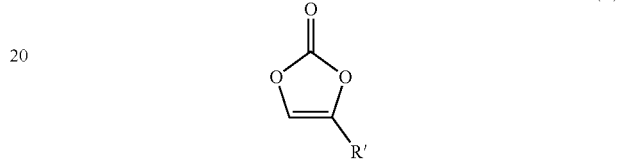

(II)

wherein R' has the meaning as given above; with a compound of general formula R—OH or a compound of general formula R—O⁻M⁺, wherein R has the meaning as given above and M⁺ is an alkaline metal cation, an alkaline earth metal cation equivalent with one positive charge, an ammonium ion or a guanidinium ion.

The term "alkyl group" is intended to denote an optionally substituted saturated linear or branched monovalent hydrocarbon radical, such as, in particular, a C1-C6 alkyl. By way of example, mention may be made of methyl, ethyl, propyl, isopropyl, butyl, t-butyl, pentyl, isopentyl and hexyl. The alkyl may be optionally substituted, e.g. with halogen, aryl, or heteroaryl. A preferred alkyl group is ethyl. The term "alkyl" also encompasses cycloalkyl groups. Cycloalkyl groups are optionally substituted cycles of saturated hydrocarbon-based groups. By way of example, mention may be made of cyclopropyl, cyclobutyl, cyclopentyl, and cyclohexyl.

The term "fluorosubstituted alkyl" is intended to denote an alkyl group wherein at least one hydrogen atom is replaced by one fluorine atom. The alkyl group can be partially or fully fluorinated. Preferred examples of fluorinated alkyl groups include trifluoromethyl, 2,2,2-trifluoroethyl, 2,2,3,3-tetrafluoropropyl and 1,1,1,3,3,3-hexafluoropropan-2-yl, especially suitable is 2,2,2-trifluoroethyl.

The term "fluorosubstituted alkyloxyalkylene" is intended to denote a fluorosubstituted alkyl group as defined above wherein at least one of the carbon atoms in the alkyl chain is replaced by an oxygen atom. Suitable examples include $CF_3$—O—$CF_2$—$CH_2$— and $CF_3$—O—$CH_2$—$CH_2$—.

Preferably, R' is hydrogen. Also preferably, R is fluorosubstituted alkyl, preferably R is trifluoromethyl, 2,2,2-trifluoroethyl, 2,2,3,3-tetrafluoropropyl or 1,1,1,3,3,3-hexafluoropropan-2-yl, more preferably R is 2,2,2-trifluoroethyl.

The compound of general formula (II) can be reacted with a suitable alcohol of general structure R—OH, for example with 2,2,2-trifluoroethanol. Alternatively, it can be reacted with a compound of general formula R—O⁻M⁺, i.e. with a suitable fluorinated alkoxy compound. Suitable M⁺ include alkali metals, e.g. Li⁺, Na⁺, K⁺ and Cs⁺. Also, suitable M⁺ include an alkaline earth metal cation equivalent with one positive charge. The term "alkaline earth metal cation equivalent with one positive charge" is to be interpreted in a way that the compound of general formula R—O⁻M⁺ results in a neutral species. Thus, a suitable "alkaline earth metal cation equivalent with one positive charge" includes $(Mg^{2+})_{1/2}$ and $(Ca^{2+})_{1/2}$, i.e. the compound of general formula R—O⁻M⁺ suitably is $(R-O^-)_2Mg^{2+}$ or $(R-O^-)_2(Ca^{2+})$. Other suitable M⁺ include ammonium ions like tetraalkylammonium ions, especially $(CH_3)_4N^+$, and guanidinium ions.

The compound of general formula R—O⁻M⁺ can be prepared and isolated in a separate chemical step and subsequently used in the inventive process. Alternatively, it can be prepared in situ before the step of reacting the compound of general formula (II) or it can be prepared continuously during the course of the reaction step. The preparation compounds of general formula R—O⁻M⁺ is generally known to the skilled artisan. In case R is CF₃, the compound can be prepared as disclosed in A. A. Kolomeitsev et al., Tetrahedron Letters, 49(3), 449-454, 2008.

Preferably, especially in case when the compound of general formula (II) is reacted with an alcohol of general structure R—OH, the step of reacting the compound of general formula (II) is carried out in the presence of a base. Suitable bases are for example hydrides like NaH or LiH, guanidines or amines. More preferably, the base is an amine; most preferably the base is a tertiary amine, specifically triethylamine.

The amount of base to be used can be stoichiometric, i.e. 1 equivalent of base is used based on the compound of general formula (II). It can also be chosen from 1.1 equivalents to 0.9 equivalents. Alternatively, the base can be used sub-stoichiometric. Preferably, the base is present in an amount of equal to or less than 25 mol %, preferably in an amount of equal to or less than 10 mol %, more preferably in an amount of between 6 mol % and 1 mol %, based on the amount of the compound of general formula (II).

The reaction step according to the present invention can be carried out in the presence of a solvent. Suitable solvents include aprotic solvents, preferably aprotic ethers like THF, monoglyme or diethyl alkyloxyalkylene. More preferably, the step of reacting the compound of general formula (II) is carried out in the absence of a solvent. In that case, the alcohol of general structure R—OH may serve as solvent, and an excess amount of alcohol may be used.

The amount of alcohol of general structure R—OH or of the compound of general formula R—O⁻M⁺ to be used can be stoichiometric, i.e. 1 equivalent of alcohol is used based on the compound of general formula (II). It can also be chosen from 1.1 equivalents to 0.9 equivalents. Alternatively, the alcohol can be used in excess. Preferably, the alcohol is present in an amount of between 1 equivalent and 20 equivalents, preferably in an amount of between 1.1 equivalent and 10 equivalents, based on the compound of general formula (II).

The temperature during the reaction step is preferably equal to or below 20° C., more preferably equal to or below 5° C., specifically around 0° C.

The resulting reaction mixture can be separated by known methods, e.g. by distillation, precipitation and/or crystallization. If desired, the reaction mixture can be contacted with water to remove water-soluble constituents. Due to the specific type of reaction, organic carbonates with a higher degree of fluorination are formed, if at all, in only very minor proportions.

In a second aspect, the present invention relates to a method for the manufacture of a compound of general formula (I),

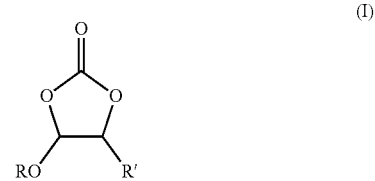

(I)

wherein R is fluorosubstituted alkyl or fluorosubstituted alkyloxyalkylene and R' is hydrogen, fluorine, alkyl, fluorosubstituted alkyl or fluorosubstituted alkyloxyalkylene; comprising a step of reacting a compound of general formula (III),

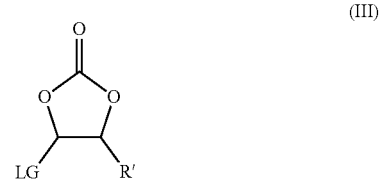

(III)

wherein R' has the meaning as given above and LG is a leaving group; with a compound of general formula R—OH or a compound of general formula R—O⁻M⁺, wherein R has the meaning as given above and M⁺ is an alkaline metal cation, an alkaline earth metal cation equivalent with one positive charge, an ammonium ion or a guanidinium ion.

The terms "alkyl", "fluorosubstituted alkyl" and "fluorosubstituted alkyloxyalkylene" shall have the same meaning as given above for the first aspect. Suitable embodiments for R, R' and M⁺ are also given above for the first aspect. Preferably, R' is a hydrogen. Also preferably, R is fluorosubstituted alkyl, preferably R is trifluoromethyl, 2,2,2-trifluoroethyl, 2,2,3,3-tetrafluoropropoxy or 1,1,1,3,3,3-hexafluoropropan-2-yl, more preferably R is 2,2,2-trifluoroethyl.

The term "leaving group" is intended to denote a molecular fragment that is suitable to depart the compound of general structure (III) with a pair of electrons in heterolytic bond cleavage. Suitable examples of leaving groups include halogen atoms such as F, Cl, Br, and I, and sulfonate esters such as tosylate or mesylate. Preferably, LG is a halogen atom, more preferably LG is Cl.

The compound of general formula (III) can be reacted with a suitable alcohol of general structure R—OH, for example with 2,2,2-trifluoroethanol. Alternatively, it can be reacted with a compound of general formula R—O⁻M⁺, i.e. with a suitable fluorinated alkoxy compound. Suitable M⁺ include alkali metals, e.g. Li⁺, Na⁺, K⁺ and Cs⁺. Also, suitable M⁺ include an alkaline earth metal cation equivalent with one positive charge. The term "alkaline earth metal cation equivalent with one positive charge" is to be interpreted in a way that the compound of general formula R—O⁻M⁺ results in a neutral species. Thus, a suitable "alkaline earth metal cation equivalent with one positive charge" includes $(Mg^{2+})_{1/2}$ and $(Ca^{2+})_{1/2}$, i.e. the compound of general formula R—O⁻M⁺ suitably is $(R-O^-)_2Mg^{2+}$ or $(R-O^-)_2(Ca^{2+})$. Other suitable M⁺ include ammonium ions like tetraalkylammonium ions, especially $(CH_3)_4N^+$, and guanidinium ions.

The compound of general formula R—O⁻M⁺ can be prepared and isolated in a separate chemical step and subsequently used in the inventive process. Alternatively, it can be prepared in situ before the step of reacting the compound of general formula (II) or it can be prepared continuously during the course of the reaction step. The preparation compounds of general formula R—O⁻M⁺ is generally known to the skilled artisan. In case R is CF₃, the compound can be prepared as disclosed in A. A. Kolomeitsev et al., Tetrahedron Letters, 49(3), 449-454, 2008.

Preferably, especially in case when the compound of general formula (II) is reacted with an alcohol of general structure R—OH, the step of reacting the compound of general formula (III) is carried out in the presence of a base. Suitable bases are for example hydrides like NaH or LiH, guanidines or amines. More preferably, the base is an amine; most preferably the base is a tertiary amine, specifically triethylamine.

The amount of base to be used can be stoichiometric, i.e. 1 equivalent of base is used based on the compound of general formula (III). It can also be chosen from 1.1 equivalents to 0.9 equivalents. Alternatively, the base can be used sub-stoichiometric. Preferably, the base is present in an amount of equal to or less than 25 mol %, preferably in an amount of equal to or less than 10 mol %, based on the amount of the compound of general formula (III).

The reaction step according to the present invention can be carried out in the presence of a solvent. Suitable solvents include aprotic solvents, preferably aprotic ethers like THF, monoglyme or diethyl alkyloxyalkylene. More preferably, the step of reacting the compound of general formula (III) is carried out in the absence of a solvent.

The temperature during the reaction step is preferably equal to or below 20° C., more preferably equal to or below 5° C., specifically around 0° C.

The resulting reaction mixture can be separated by known methods, e.g. by distillation, precipitation and/or crystallization. If desired, the reaction mixture can be contacted with water to remove water-soluble constituents. Due to the specific type of reaction, organic carbonates with a higher degree of fluorination are formed, if at all, in only very minor proportions.

In a third aspect, the present invention relates to compounds of general formula (IV),

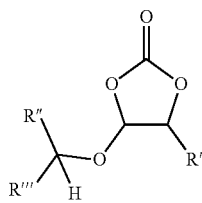

(IV)

wherein R' is hydrogen, fluorine, alkyl, fluorosubstituted alkyl or fluorosubstituted alkyloxyalkylene; R" is fluorosubstituted alkyl or fluorosubstituted alkyloxyalkylene and R''' is hydrogen, fluorine, alkyl, fluorosubstituted alkyl or fluorosubstituted alkyloxyalkylene. The terms "alkyl", "fluorosubstituted alkyl" and "fluorosubstituted alkyloxyalkylene" shall have the same meaning as given above for the first aspect.

Preferably, R' is hydrogen.

R" and R''' can be the same or different. If R" and R''' are the same they are preferably trifluoromethyl.

Preferably, R" and R''' are different. More preferably, R''' is hydrogen or trifluoromethyl, most preferably hydrogen. More preferably, R" is trifluoromethyl, 2,2,2-trifluoroethyl, 2,2,3,3-tetrafluoropropyl or 1,1,1,3,3,3-hexafluoropropan-2-yl, most preferably trifluoromethyl.

Preferred compounds of the invention are 4-(2,2,2-trifluoroethoxy)-1,3-dioxolan-2-one, 4-(1,1,1,3,3,3-hexafluoropropan-2-yloxy)-1,3-dioxolan-2-one and 4-(2,2,3,3-tetrafluoropropoxy)-1,3-dioxolan-2-one, specifically 4-(2,2,2-trifluoroethoxy)-1,3-dioxolan-2-one.

The present invention also relates to the use of a compound of general formula (IV) as a solvent additive or as solvent for lithium ion batteries, lithium air batteries, lithium sulphur batteries, supercapacitors or hybrid supercapacitors.

In a fourth aspect, the present invention concerns a solvent composition for lithium ion batteries, lithium air batteries, lithium sulfur batteries, supercapacitors or hybrid supercapacitors, comprising at least one solvent useful for lithium ion batteries, further comprising at least one compound of general formula (IV) as described above.

The compounds of general formula (IV) are advantageously applied in solvent compositions or in electrolyte compositions together with at least one suitable solvent known to the expert in the field of lithium ion batteries or supercapacitors. For example, organic carbonates, but also lactones, formamides, pyrrolidinones, oxazolidinones, nitroalkanes, N,N-substituted urethanes, sulfolane, dialkyl sulfoxides, dialkyl sulfites, acetates, nitriles, acetamides, glycol ethers, dioxolanes, dialkyloxyethanes, trifluoroacetamides, are very suitable as solvents.

Preferably, the aprotic organic solvent is selected from the group of dialkyl carbonates (which are linear) and alkylene carbonates (which are cyclic), ketones, and formamides. Dimethyl carbonate, diethyl carbonate, methyl ethyl carbonate, cyclic alkylene carbonates, e.g. ethylene carbonate, propylene carbonate, and vinylidene carbonate, are examples of suitable solvents.

Fluorosubstituted compounds different from the compounds of general formula (I) as described above, for example, fluorosubstituted ethylene carbonates, polyfluorosubstituted dimethyl carbonates, fluorosubstituted ethyl methyl carbonates, and fluorosubstituted diethyl carbonates are other suitable solvents or suitable additional additives in the electrolytic compositions.

Other suitable additional additives useful in the electrolyte compositions according to the present invention are those described in WO2007/042471.

For suitable components, including solvent, co-solvent, electrolyte salt, and additive, reference can be made to those described in WO 2016/097129 which is incorporated herein by its entirety.

In a fifth aspect, present invention concerns an electrolyte composition for lithium ion batteries, lithium air batteries, lithium sulfur batteries, supercapacitors or hybrid supercapacitors, comprising at least one compound according to the invention, at least one solvent useful for lithium ion batteries or supercapacitors and at least one electrolyte salt.

The electrolyte composition, further to the at least one compound of general formula (I), comprises at least one dissolved electrolyte salt. Such salts have the general formula $M_aA_b$. M is a metal cation, and A is an anion. The overall charge of the salt $M_aA_b$ is 0. M is preferably selected from Li⁺ and NR₄⁺. Preferred anions are $PF_6^-$, $PO_2F_2^-$, $AsF_6^-$, $BF_4^-$, $ClO_4^-$, $N(CF_3SO_2)_2^-$, $N(FSO_2)_2^-$, and $N(i-C_3F_7SO_2)_2^-$.

Preferably, M is Li⁺. Especially preferably, M is Li⁺ and the solution comprises at least one electrolyte salt selected from the group consisting of $LiBF_4$, $LiClO_4$, $LiAsF_6$, $LiPF_6$, $LiPO_2F_2$, $LiN(CF_3SO_2)_2$, $LiN(FSO_2)_2$ and $LiN(i\text{-}C_3F_7SO_2)_2$. Lithium bis(oxalato)borate can be applied as an additional additive. The concentration of the electrolyte salt is preferably between 0.8 and 1.2 molar, more preferably 1.0 molar. Often, the electrolyte composition may comprise $LiPF_6$ and $LiPO_2F_2$.

The compounds of formula (I) can be introduced into the electrolyte composition separately or in the form of a mixture with other compounds, e.g. as a mixture with one or more solvents used in the electrolyte composition or together with the electrolyte salt or together with other additives.

In a sixth aspect, the present invention relates to lithium ion batteries, lithium air batteries and lithium sulfur batteries comprising a solvent composition as outlined above or an electrolyte composition as outlined above.

The compounds according to this invention may advantageously be used as a solvent, a solvent additive or a co-solvent in a concentration from 1 to 20 wt %, preferably from 3 to 10 wt %, more preferably between 4 and 6 wt % and most preferably around 5 wt % relative to the total weight of the electrolyte composition. Alternatively, the concentration of the compound may be, in particular when the compound is intended to be used as solvent or co-solvent in the electrolyte composition, from 20 wt % to 60 wt %, preferably from 20 wt % to 50 wt %, more preferably from 25 wt % to 40 wt %, relative to the total weight of the electrolyte composition.

Accordingly, another aspect of the invention concerns the use of a compound according to this invention in an electrolyte composition, in an electrolyte composition for Li ion batteries, Li air batteries or Li sulfur batteries, wherein the concentration of the compound according to the invention is from 1 to 20 wt %, preferably from 3 to 10 wt %, more preferably between 4 and 6 wt % and most preferably around 5 wt %; relative to the total weight of the electrolyte composition. Alternatively, the concentration is from 0.1 wt % to 1.0 wt %, specifically around 0.5 wt %. Further alternatively, the concentration can be from 20 to 60 wt %, preferably from 20 wt % to 50 wt %, more preferably from 25 wt % to 40 wt %, relative to the total weight of the electrolyte composition. The inventive electrolyte is preferably a liquid anhydrous electrolyte, also preferably it is a gel-type electrolyte.

Another aspect of the present invention concerns a particular electrolyte composition comprising the compounds of the invention. Such electrolyte composition comprises:
at least one electrolyte salt,
at least one solvent, and
at least one additive,
wherein the at least one solvent comprises 70 to 90 vol % of at least one linear carbonate and 10 to 30 vol % of at least one cyclic carbonate, relative to the total volume of the solvent,
characterized in that the cyclic carbonate comprises the compound of the present invention.

The amount of the compound of the invention in the total volume of the solvent in the electrolyte composition of this aspect may be from 10 to 30 vol %, preferably 10 to 20 vol %.

Examples of the linear carbonate particularly preferred in the electrolyte composition of this aspect include dimethyl carbonate, diethyl carbonate, ethyl methyl carbonate, and any combination thereof.

Examples of the cyclic carbonate particularly preferred in the electrolyte composition of this aspect include ethylene carbonate, propylene carbonate, and combination thereof.

The electrolyte composition according to this aspect may further comprise one or more additives. Particular type of such additive is SEI-forming compound. In the present invention, the "SEI-forming compound" is understood to denote in particular the chemical compound included in electrolyte composition of battery, the compound which generates passive layer on the surface of electrode(s) of battery. Examples of the SEI-forming compound particularly preferred in the present invention include monofluoro ethylene carbonate, vinylene carbonate, vinyl ethylene carbonate, ethylene sulfite, and vinyl ethylene sulfite, but the present invention is not limited thereto. The amount of the SEI-forming compound in the electrolyte composition may be from 0.1 to 10 wt %, preferably from 1 to 5 wt %, more preferably from 3 to 5 wt %, relative to the total weight of the electrolyte composition. Another type of such additive is swelling inhibiting compound. In the present invention, the "swelling inhibiting compound" is understood to denote in particular the chemical compound included in electrolyte composition of battery, the compound which suppresses a generation of gas in battery system by decomposition thereof. Examples of the swelling inhibiting compound particularly preferred in the present invention include 4,4-difluoro ethylene carbonate (trans and cis), propane sultone, fluoro propane sultone, propene sultone, bisphenols, dimethyl furan, and N-acetyl caprolactam, but the present invention is not limited thereto. The amount of the swelling inhibiting compound in the electrolyte composition may be from 0.1 to 5 wt %, preferably from 0.5 to 3 wt %, more preferably from 1 to 2 wt %, relative to the total weight of the electrolyte composition.

In the present invention, the SEI-forming compounds and the swelling inhibiting compounds can be used in the electrolyte system for battery in general.

As to the particular examples and amount of the electrolyte salt, reference can be made to the above-explained section for the electrolyte salt.

Preferably, the electrolyte composition of this aspect of the present invention further comprises at least one SEI-forming compound and at least one swelling inhibiting compound. Surprisingly, the present inventors found that such electrolyte composition may exhibit excellent thermal stability, in particular at least one of outstanding cycle performance and storage property at high temperature, such as around 60° C. or above.

Lithium ion batteries comprises an anode, preferably an anode made from carbon on a copper foil, a cathode, preferably a cathode made from lithium metal oxides on an aluminum foil, a separator, preferably a separator made from an insulating polymer, and a solvent composition or an electrolyte composition as described above. The foils used for anode and cathode are also called current collectors.

Should the disclosure of any patents, patent applications, and publications which are incorporated herein by reference conflict with the description of the present application to the extent that it may render a term unclear, the present description shall take precedence.

The invention will now be further described in examples without intending to limit it.

EXAMPLES

Example 1: General Procedure for Synthesis Via Substitution

Lithium (0.69 g, 100 mmol) was dissolved in a solution of the corresponding fluorinated alcohol (100 mmol) in 50 mL Et₂O. The resulting solution was added to a solution of 4-chloroethylene carbonate (12.9 g, 105 mmol) in 50 mL Et₂O at −10° C. over the course of 15 min. Shortly after the start of the addition, a white precipitate formed. The reaction mixture was stirred at 0° C. for 1 h and then at room temperature overnight. The reaction was quenched with water and the aqueous layer was extracted with EtOAc. The organic layer was washed with water and brine and dried over Na₂SO₄. The crude product was distilled in vacuum (0.05 mmHg) to obtain a clear viscous liquid.

Example 1a: Synthesis of
4-(2,2,3,3-tetrafluoropropoxy)-1,3-dioxolan-2-one

Yield: 80.2%. 1H NMR (400 MHz, CDCl3) δ 5.88 (tt, J=53.0, 4.1 Hz, 1H), 5.72 (dd, J=5.6, 2.3 Hz, 1H), 4.54 (dd, J=10.0, 5.6 Hz, 1H), 4.32 (dd, J=10.0, 2.3 Hz, 1H), 4.20 (td, J=14.0, 1.9 Hz, 1H), 4.02 (td, J=12.2, 2.1 Hz, 1H). 13C NMR (100 MHz, CDCl3): δ 153.4, 123.0 (d, J=277.6 Hz), 99.5, 70.1, 66.1 (d, J=35.5 Hz). 19F NMR (376 MHz, CDCl3) δ −123.94 (dtq, J=278.9, 13.0, 3.3 Hz, 1F), −124.81 (dtq, J=278.9, 11.9, 2.9 Hz, 1F), −137.58 (ddq, J=304.3, 52.9, 2.6 Hz, 1F), −138.82 (ddq, J=304.5, 53.2, 3.2 Hz, 1F).

Example 1b:
4-(2,2,2-trifluoroethoxy)-1,3-dioxolan-2-one

Yield: 74.7%. 1H NMR (400 MHz, CDCl3): δ 5.74 (dd, J=5.6, 2.2 Hz, 1H), 4.55 (dd, J=10.0, 5.6 Hz, 1H), 4.34 (dd, J=10.0, 2.3 Hz, 1H), 4.15 (dq, J=12.5, 8.7 Hz, 1H), 4.03 (dq, J=12.4, 8.3 Hz, 1H). 13C NMR (100 MHz, CDCl3): δ 153.4, 123.0 (d, J=277.6 Hz), 99.5, 70.1, 66.1 (d, J=35.5 Hz). 19F NMR (376 MHz, CDCl3): δ −74.28 (d, J=8.3 Hz).

Example 2a: Synthesis of
4-(2,2,2-trifluoroethoxy)-1,3-dioxolan-2-one

To a vigorously stirred solution of vinylidene carbonate (172.1 g, 127 mL, 2 mol) in 140 mL monoglyme, a mixture of 292.3 g (211.2 mL, 2.92 mol) 2,2,2-trifluoroethanol and 295.5 g (404.8 mL, 2.92 mol) triethylamine was added at −5° C. under inert atmosphere. Afterwards the resulting mixture was stirred at 2 to 4° C. for 7 hours and then at room temperature overnight. The reaction mixture was diluted with 2 L diethyl ether and the suspension formed was filtered. The filtrate was evaporated using a rotary evaporator and the residue was distilled under reduced pressure (0.5 mmHg) to yield 330.5 g (88.8%) of a yellowish liquid with a boiling point of 78-82° C./0.5 mmHg. 1H NMR (CDCl3, 400 MHz) δ: 4.06 (ddd, 2H, 2JHH 30.1 Hz, 3JHH 8.4 Hz, 3JHH 7.8 Hz, HB), 4.32 (m, 2H, 4JHH 2.4 Hz, 3JHF 8.7 Hz, HC), 5.73 (dd, 1H, 3JHH 7.9 Hz, 3JHH 8.3 Hz, HA); 13C NMR (CDCl3) δ: 66.1 (q, 1C, 2JCF 35.5 Hz, CH2), 70.1 (s, 1C, O—CH2), 99.6 (s, 1C, O—CH), 123.0 (q, 1C, 1JCF 278.0 Hz, CF3), 153.5 (s, 1C, C(O)); 19F NMR (CDCl3) δ: −74.5 (t, 3F, 3JFH 8.7 Hz, CF3). MS: (ESI, positiv, MeOH) m/z 186 [M+].

Example 2b: Synthesis of 4-(1,1,1,3,3,3-hexafluoropropan-2-yloxy)-1,3-dioxolan-2-one 4-(1,1,1,3,3,3-Hexafluoropropan-2-yloxy)-1,3-dioxolan-2-one was obtained according to the procedure described for example 2a using 43.1 g (31.8 mL, 0.5 mol) vinylidene carbonate, 45 mL monoglyme, 122.6 g (76.4 mL, 0.73 mol) 1,1,1,3,3,3-hexafluoropropan-2-ol and 73.9 g (101.2 mL, 0.73 mol) triethylamine as a yellowish liquid with a boiling point of 88-91° C./0.5 mmHg in a yield of 98.4 g (77.4%). 1H-NMR (CDCl3, 400 MHz) δ: 4.47 (m, 1H, 4JHH 1.4 Hz, HC), 4.59 (ABX'-System, 2H, 2JAB 20.5 Hz, 3JAX' 5.9 Hz, 3JBX' 5.1 Hz, HB), 5.89 (m, 1H, 3JHH 5.1 Hz, HA). 13C NMR (CDCl3) δ: 70.2 (s, 1C, O—CH2), 73.1 (sep, 1C, 2JCF 33.6 Hz, CH), 99.4 (s, 1C, O—CH), 120.3 (q, 1C, 1JCF 285.6 Hz, CF3), 121.1 (q, 1C, 1JCF 282.8 Hz, CF3), 152.7 (s, 1C, C(O)). 19F NMR (CDCl3) δ: −73.84 (m, 3F, CF3), −73.58 (m, 3F, CF3). MS: (ESI, positiv, MeCN) m/z 254 [M+].

Example 2c: Synthesis of
4-(2,2,3,3-tetrafluoropropoxy)-1,3-dioxolan-2-one 4-(2,2,3,3-tetrafluoropropoxy)-1,3-dioxolan-2-one was obtained according to the procedure described for example 2a using 43.1 g (31.8 mL, 0.5 mol) vinylidene carbonate, 24 mL monoglyme, 79.3 g (53.4 mL, 0.6 mol) 2,2,3,3-tetrafluoropropan-1-ol and 60.7 g (83.2 mL, 0.6 mol) triethylamine as a yellowish liquid with a boiling point of 128-132° C./0.5 mmHg in a yield of 83.1 g (76.2%). 1H NMR (CDCl3, 400 MHz) δ: 4.11 (ddd, 2H, 2JHH 71.5 Hz, 3JHH 11.9 Hz, 3JHH 2.0 Hz, HB), 4.31 (dd, 1H, 4JHH 2.2 Hz, 3JHF 10.1 Hz, HC), 4.54 (dd, 1H, 3JHH 5.6 Hz, 3JHH 10.1 Hz, HC), 5.71 (dd, 1H, 3JHH 2.2 Hz, 3JHH 5.6 Hz, HA), 5.88 (tt, 1H, 3JHF 4.4 Hz, 2JHF 53.0 Hz, CF2H). 13C NMR (CDCl3) δ: 65.6 (t, 1C, 2JCF 27.9 Hz, CH2), 70.1 (s, 1C, O—CH2), 99.7 (s, 1C, O—CH), 109.2 (tt, 1C, 2JCF 35.6 Hz, 1JCF 249.5 Hz, CF2H), 114.2 (tt, 1C, 2JCF 27.9 Hz, 1JCF 249.5 Hz, CF2), 153.4 (s, 1C, C(O)). 19F NMR (CDCl3) δ: −138.34 (ABX-System, 2F, 2JAB 306.3 Hz, 2JAX 50.6 Hz, 2JBX 56.4 Hz, CF2H), −124.49 (ABX2-System, 2F, 2JAB 280.3 Hz, 3JAX 2.9 Hz, 3JBX 2.9 Hz, CF2). MS: (ESI, positiv, MeCN) m/z 218 [M+].

Example 2d: Solvent-Free Synthesis of
4-(2,2,2-trifluoroethoxy)-1,3-dioxolan-2-one 48.9 g 2,2,2-trifluoroethanol was added dropwise to a mixture of vinylene carbonate (42.8 g, 1 equivalent) and triethylamine (5.2 g, 0.1 equivalent) at 0° C. over a period of 90 minutes. The mixture was stirred at 0° C. for one additional hour. After removing the volatiles on a rotary evaporator, the residue was distilled under reduced pressure to yield 66.3 g (72%) 4-(2,2,2-trifluoroethyl)-ethylene carbonate as a colorless clear liquid.

Example 3: Construction of Battery Cell

A pouch full cell consisting of [LiCoO₂:Super-P® (conductive carbon black obtainable from MMM Carbon, Belgium):PVdF (Solef® 5130 from Solvay Specialty Polymers) binder=92:4:4 (wt. %)] as positive electrode and [SCMG-AR® (artificial graphite obtainable from Showa Denko): Super-P® (conductive carbon black obtainable from MMM Carbon, Belgium):PVdF (Solef® 5130 from Solvay Specialty Polymers) binder=90:4:6 (wt. %)] as negative electrode was prepared. Polyethylene was used as separator. The preparation of the pouch cells consisted of the following steps in that order: (1) mixing, (2) coating & Drying (3) pressing, (4) slitting, (5) Tap welding, (6) Assembly, (7) Pouch 2-side sealing, (8) Electrolyte filling, and (9) Vacuum sealing. The design capacity of cells is about 50 mAh (Size 5 cm×5 cm).

Example 4: Preparation of Electrolyte
Compositions

Battery grade 1 M LiPF₆ in ethylene carbonate (EC)/ dimethyl carbonate (DMC) (½, v/v) was used as the base electrolyte solution under dry room atmosphere. The following electrolyte compositions were used (TFEEC=4-(2,2,2-trifluoroethoxy)ethylene carbonate).

|  | Additive |
|---|---|
| Example A (Comparative) | None |
| Example B (Inventive) | 0.1% TFEEC |
| Example C (Inventive) | 0.5% TFEEC |

Example 5: Cycle Performance Test

Charge and discharge cycling tests of the lithium-ion cells were conducted under 1.0 C rate over a voltage range of 3.0-4.4 V. This cycle was repeated 300 cycles at 23° C. The ratio of the discharge capacity at the 300th cycle to that at the first cycle was defined as the cycle retention. FIG. 1 shows the results of example 5 and the advantageous effects of the inventive compounds.

Example 6: Preparation of Dry Cells

A 20-stacked dry cell consisting of [LiCoO$_2$:LiNCA=1:1] as positive electrode and [Artificial graphite] as negative electrode was prepared. Polyolefin was used as separator. All the components were placed in Al polymer pouch with compact sealing except one side to electrolyte injection.

Before electrolyte injection, the dry cell was vacuum dried at 55° C. for 4 days to avoid moisture contamination.

The next steps of cell fabrication were as follows: (1) Electrolyte filling, (2) Vacuum and venting, (3) Vacuum sealing (4) Charging to SOC30 (state of charge), (5) Aging at RT, (6) Degassing, (7) vacuum sealing (8) Discharge capacity check. The design capacity of cells is 950 mAh (width: 38 mm, depth: 3.5 mm, height: 62 mm, 383562 type cells).

Example 7: Preparation of Electrolyte Compositions

Battery grade 1.2 M LiPF$_6$ in ethylene carbonate (EC)/ethyl methyl carbonate (EMC)/dimethyl carbonate (DMC) (3/4/3, v/v) was used as the base electrolyte solution under dry room atmosphere. The following electrolyte compositions as shown in Table 1 were used:

TABLE 1

| Electrolyte formulations | | | | | |
|---|---|---|---|---|---|
| Additives (wt. %) | | Solvent (vol. %) | | | |
| F1EC | DFEC | EC | EMC | DMC | TFEEC |
| Example D (comparative) 5 | 2 | 30 | 40 | 30 | — |
| Example E (Inventive) 5 | 2 | 20 | 40 | 30 | 10 |

F1EC = Fluoro ethylene carbonate
DFEC = trans-difluoro ethylene carbonate
TFEEC = 4-(2,2,2-trifluoroethoxy)ethylene carbonate
F1EC and DFEC are used as additives for SEI formation and gas reduction.

Example 8: Cycle Performance Test at High Temperature (45° C.)

Figure 2:
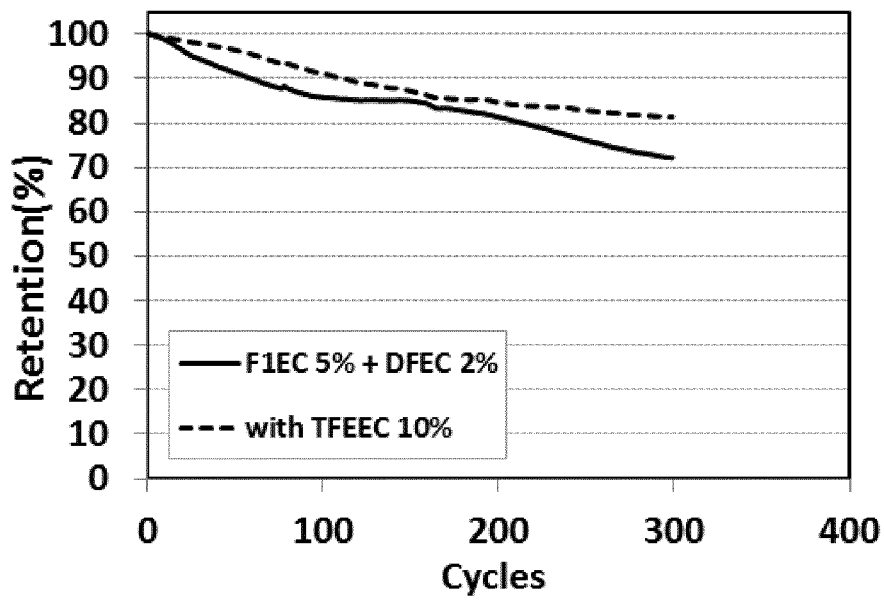
FIG. 2 shows the cycle performance of LCO/NCA+ Graphite cells at 45° C. as described in Example 8.

Charge and discharge cycling tests of the lithium-ion cells were conducted under 1.0 C (charge) and 2.0 C (discharge) rate over a voltage range of 3.0-4.2 V. This cycle was repeated 300 cycles at 45° C. The ratio of the discharge capacity at the 300$^{th}$ cycle to that at the first cycle was defined as the cycle retention. FIG. 2 shows the results of example 8 and the advantageous effects of the inventive compounds.

|  | 1$^{st}$ discharge capacity (mAh) | Retention (%) |
|---|---|---|
| Example D | 880.1 | 72.1 |
| Example E | 883.5 | 81.4 |

Example 9: Storage Test at 60° C.

Figure 3:
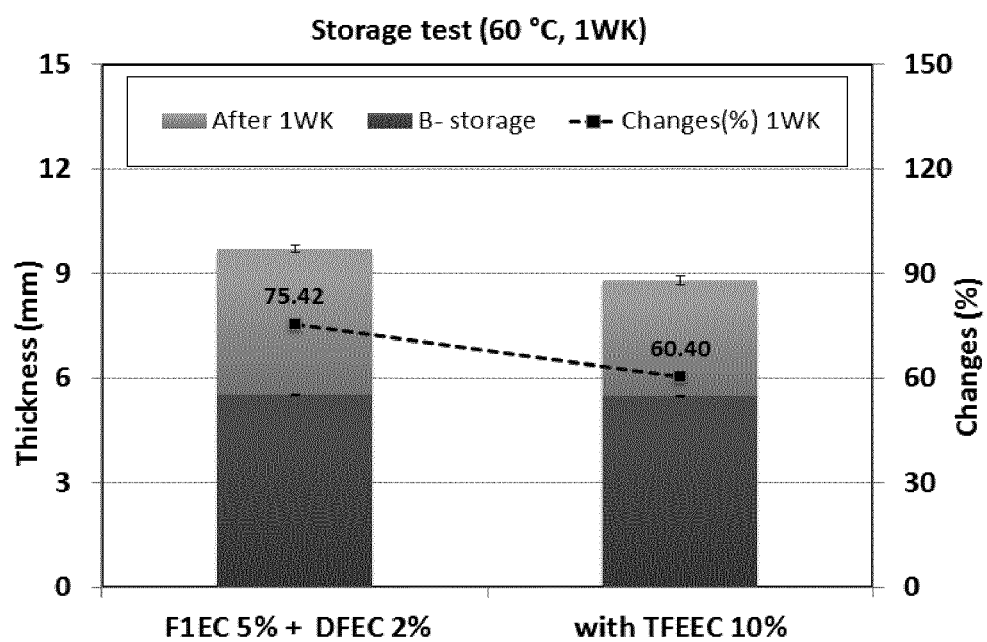
FIG. 3 shows the thickness change (%) of LCO/NCA+ Graphite cells after storage test at 60° C. as described in Example 9.

The storage test is measuring the cell thickness change (%) after storing at high temperature. The manufactured battery was initially charged/discharged at room temperature and then charged/discharged three times at a 1.0 C current rate, which was terminated at the final time in a charged state (4.2V). The battery in a charged state is tested to measure its thickness while storing at 60° C. chamber after 1 week. The measured result is shown in FIG. 3.

The invention claimed is:

1. A method for the manufacture of a compound of general formula (I),

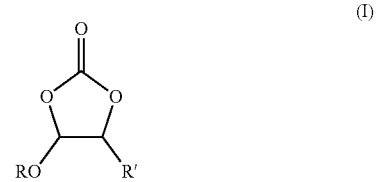

(I)

wherein R is fluorosubstituted alkyl or fluorosubstituted alkyloxyalkylene and R' is hydrogen, fluorine, alkyl, fluorosubstituted alkyl or fluorosubstituted alkyloxyalkylene;
the method comprising a step of reacting a compound of general formula (II),

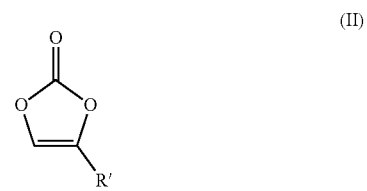

(II)

wherein R' has the meaning as given above; with a compound of general formula R—OH or a compound of general formula R—O$^-$M$^+$, wherein R has the meaning as given above and M$^+$ is an alkali metal cation, an ammonium ion or a guanidinium ion, or a compound of general formula (R—O$^-$)$_2$M$^+$, wherein R has the meaning as given above and M$^+$ is an alkaline earth metal cation.

2. The method according to claim 1 wherein R' is hydrogen.

3. The method according to claim 1 wherein R is fluorosubstituted alkyl.

4. The method according to claim 1 wherein the step of reacting the compound of general formula (II) is carried out in the presence of a base.

5. The method according to claim 4 wherein the base is present in an amount of equal to or less than 25 mol %, based on the amount of the compound of general formula (II).

6. The method according to claim 1 wherein the step of reacting the compound of general formula (II) is carried out in the absence of a solvent.

7. A method for the manufacture of a compound of general formula (I),

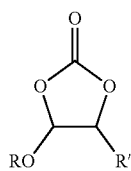
(I)

wherein R is fluorosubstituted alkyl or fluorosubstituted alkyloxyalkylene and R' is hydrogen, fluorine, alkyl, fluorosubstituted alkyl or fluorosubstituted alkyloxyalkylene;

the method comprising a step of reacting a compound of general formula (III),

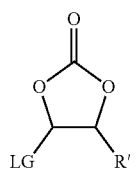
(III)

wherein R' has the meaning as given above and LG is a leaving group;

with a compound of general formula R—OH or a compound of general formula R—O⁻M⁺, wherein R has the meaning as given above and M⁺ is an alkali metal cation, an ammonium ion or a guanidinium ion, or a compound of general formula (R—O⁻)₂M⁺, wherein R has the meaning as given above and M⁺ is an alkaline earth metal cation.

8. The method according to claim 7 wherein R' is hydrogen.

9. The method according to claim 7 wherein R is fluorosubstituted alkyl.

10. The method according to claim 7 wherein LG is a halogen atom.

11. A compound of general formula (IV),

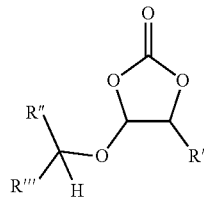
(IV)

wherein R' is hydrogen, fluorine, alkyl, fluorosubstituted alkyl or fluorosubstituted alkyloxyalkylene; R'' is fluorosubstituted alkyl or fluorosubstituted alkyloxyalkylene and R''' is hydrogen, fluorine, alkyl, fluorosubstituted alkyl or fluorosubstituted alkyloxyalkylene.

12. The compound of claim 11 wherein R' is hydrogen.

13. The compound of claim 11 wherein R'' is trifluoromethyl, R''' is hydrogen and the compound is 4-(2,2,2-trifluoroethoxy)-1,3-dioxolan-2-one.

14. An electrolyte composition for lithium ion batteries, lithium air batteries, lithium sulfur batteries, supercapacitors or hybrid supercapacitors, the composition comprising at least one compound according to claim 11, at least one solvent useful for lithium ion batteries or supercapacitors and at least one electrolyte salt.

15. The electrolyte composition according to claim 14, further comprising at least one SEI-forming chemical compound and at least one swelling inhibiting compound.

16. The electrolyte composition according to claim 14, wherein the at least one solvent comprises 70 to 90 vol % of at least one linear carbonate and 10 to 30 vol % of at least one cyclic carbonate, relative to the total volume of the solvent,
and wherein at least a part of the cyclic carbonate is the compound of general formula (IV).

17. A lithium ion battery, a lithium air battery, a lithium sulfur battery, a supercapacitor or a hybrid supercapacitor comprising at least one compound according to claim 11.

18. The method according to claim 3 wherein R is trifluoromethyl, 2,2,2-trifluoroethyl, 2,2,3,3-tetrafluoropropoxy or 1,1,1,3,3,3-hexafluoropropan-2-yl.

19. The method according to claim 18 wherein R is 2,2,2-trifluoroethyl.

20. A lithium ion battery, a lithium air battery, a lithium sulfur battery, a supercapacitor or a hybrid supercapacitor comprising the electrolyte composition of claim 14.

* * * * *